United States Patent
Funnell et al.

(10) Patent No.: US 12,235,150 B2
(45) Date of Patent: Feb. 25, 2025

(54) AUTOMATIC FLUID FLOW SYSTEM WITH LATCH CONNECTION

(71) Applicant: C. R. Bard, Inc., Franklin Lakes, NJ (US)

(72) Inventors: Emelia Funnell, Milton, GA (US); Jason Jishen Cheng, Avondale Estates, GA (US); Rohit Sinha, Lawrenceville, GA (US); Michal Tourchak, Atlanta, GA (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 0 days.

(21) Appl. No.: 18/537,483

(22) Filed: Dec. 12, 2023

(65) Prior Publication Data

US 2024/0102847 A1   Mar. 28, 2024

Related U.S. Application Data

(63) Continuation of application No. 17/380,846, filed on Jul. 20, 2021, now Pat. No. 11,867,554.

(60) Provisional application No. 63/054,682, filed on Jul. 21, 2020.

(51) Int. Cl.
| | |
|---|---|
| *G01G 21/23* | (2006.01) |
| *A61B 5/20* | (2006.01) |
| *A61F 5/44* | (2006.01) |
| *G01F 23/20* | (2006.01) |
| *G01G 17/04* | (2006.01) |

(Continued)

(52) U.S. Cl.
CPC ............. *G01G 21/23* (2013.01); *A61B 5/208* (2013.01); *A61F 5/44* (2013.01); *G01F 23/20* (2013.01); *G01G 17/04* (2013.01); *G01G 19/18* (2013.01); *G01G 21/28* (2013.01)

(58) Field of Classification Search
CPC ........ G01G 17/10; G01G 19/14; G01G 19/18; G01G 21/23; G01G 21/28; G01F 23/20; G01F 23/205; A61B 5/208; A61F 5/44
See application file for complete search history.

(56) References Cited

U.S. PATENT DOCUMENTS

| 8,076,596 B2 | 12/2011 | Burkart |
| 9,995,619 B2 * | 6/2018 | Parker .................... G01G 19/18 |
| 10,444,060 B2 | 10/2019 | Parker et al. |

(Continued)

OTHER PUBLICATIONS

U.S. Appl. No. 17/380,846, filed Jul. 20, 2021 Non Final Office Action dated Jun. 13, 2023.

(Continued)

*Primary Examiner* — Randy W Gibson
(74) *Attorney, Agent, or Firm* — Rutan & Tucker LLP (57) ABSTRACT

Embodiments disclosed herein are directed to apparatus and methods for automatic fluid flow system connectors. The system generally includes a load cell interface coupled to a console and a ring connector coupled to a fluid collection system. The ring connector can be releasably engaged with the load cell using an engagement structure such as a latch, locking arm, or spring clip mechanism. The ring connector and load cell can include electrical contacts configured to engage along an axis that extends perpendicular to a surface that the electrical contacts are disposed on. Advantageously, reduced wear on the electrical contacts should extend the usable life of the system.

26 Claims, 8 Drawing Sheets

(51) Int. Cl.
  *G01G 19/18*  (2006.01)
  *G01G 21/28*  (2006.01)

(56) References Cited

U.S. PATENT DOCUMENTS

| | | |
|---|---|---|
| 11,022,482 B2 | 6/2021 | Parker et al. |
| 11,602,248 B2 | 3/2023 | Steinmetz et al. |
| 2022/0018692 A1 | 1/2022 | Tourchak et al. |
| 2022/0026001 A1 | 1/2022 | Cheng et al. |
| 2022/0026261 A1 | 1/2022 | Funnell et al. |
| 2023/0084476 A1 | 3/2023 | Robichaud et al. |

OTHER PUBLICATIONS

U.S. Appl. No. 17/380,846, filed Jul. 20, 2021 Notice of Allowance dated Sep. 6, 2023.

\* cited by examiner

AUTOMATIC FLUID FLOW SYSTEM WITH LATCH CONNECTION

PRIORITY

This application is a continuation of U.S. patent application Ser. No. 17/380,846, filed Jul. 20, 2021, now U.S. Pat. No. 11,867,554, which claims the benefit of priority to U.S. Provisional Application No. 63/054,682, filed Jul. 21, 2020, which is incorporated by reference in its entirety into this application.

SUMMARY

Briefly summarized, embodiments disclosed herein are directed to automatic fluid flow system connectors and the like. In order to maintain a high accuracy of fluid flow monitoring, automatic fluid flow systems can determine a change in fluid volume by detecting a change in weight of a fluid collection system, over time. These detection systems rely on precise weight measurements to provide high accuracy of fluid flow in low-flow situations. As such, interface mechanisms configured to engage the fluid collection system with the automatic fluid flow system require a secure fit to ensure the downward forces, or changes thereof, are accurately transferred to the automatic fluid flow system. Further, the interface mechanisms must sustain repeated engagements and disengagements as different fluid collection systems are coupled or uncoupled to the automatic fluid flow system.

Disclosed herein is an automatic fluid flow measuring system including, a ring connector configured to be coupled to a fluid collection system and including a first electrical contact disposed on a first surface, a load cell including a second electrical contact disposed on a second surface, the load cell configured to engage and retain the ring connector such that the first electrical contact engages the second electrical contact along an axis extending perpendicular to both the first surface and the second surface, and an engagement structure engaging a side surface of one of the ring connector or the load cell and configured to releasably secure the ring connector to the load cell.

In some embodiments, wherein the engagement structure includes a latch hingedly coupled to one of the ring connector or the load cell and rotatable between an unlocked position and a locked position, the latch engaging a flange in the locked position to releasably secure the ring connector to the load cell. In some embodiments, the latch engages the flange in one of an interference fit, press-fit, or snap-fit engagement. In some embodiments, the flange extends along a portion of a side surface of the load cell and extends parallel to the second surface of the load cell.

In some embodiments, the ring connector includes a protrusion, extending from a rear surface thereof, and wherein the load cell includes a recess disposed on a front surface thereof and configured to receive the protrusion. In some embodiments, the load cell includes a pair of guide plates extending from a side surface of the load cell and configured to receive the latch therebetween. In some embodiments, the automatic fluid flow measuring system further includes an O-ring configured to engage both the ring connector and the load cell in the locked configuration to provide a fluid-tight seal therebetween. In some embodiments, the O-ring extends annularly around one of a ring connector electrical contact or a load cell electrical contact.

In some embodiments, the engagement structure includes a first locking arm and a second locking arm slidably engaged with the load cell and transitionable between a locked position and an unlocked position. In some embodiments, the first locking arm and a second locking arm are slidable along an axis extending parallel to the second surface. In some embodiments, the automatic fluid flow measuring system further includes a biasing member configured to bias the first locking arm and the second locking arm to the locked position. In some embodiments, the automatic fluid flow measuring system further includes an actuator configured to release the first locking arm and the second locking arm and allow the biasing member to transition the first locking arm and the second locking arm from the unlocked position to the locked position.

In some embodiments, the actuator is disposed on the second surface and configured to be actuated by the first surface engaging the second surface. In some embodiments, the actuator includes one of a push button, pressure transducer, optical transducer, magnetic switch, electro-magnetic actuator, solenoid, or a radio-frequency tag. In some embodiments, the automatic fluid flow measuring system further includes a first release arm and a second release arm slidably engaged with the load cell and configured to transition the a first locking arm and a second locking arm from a locked position to an unlocked position. In some embodiments, the automatic fluid flow measuring system further includes a seat extending from a lower surface of the load cell and configured to support a bottom surface of the ring connector to transfer a downward force from the ring connector to the load cell.

Also disclosed is an automatic fluid flow measuring system including, a ring connector having a peg extending from a front surface and configured to be coupled to a fluid collection system, the ring connector including a first electrical contact disposed on a first surface, a load cell including a cradle configured to engage a portion of the ring connector and including a second electrical contact disposed on a second surface, the first electrical contact engaging the second electrical contact along an axis extending perpendicular to both the first surface and the second surface.

In some embodiments, the ring connector includes a spring clip slidable between a locked position and an unlocked position, the spring clip engaging the cradle to releasably secure the ring connector to the load cell. In some embodiments, the ring connector includes a biasing member configured to bias the spring clip towards the locked position. In some embodiments, the ring connector includes an actuator configured to transition the spring clip from a locked position to an unlocked position. In some embodiments, the cradle includes a seat extending from the second surface of the load cell and configured to support a bottom surface of the ring connector to transfer a downward force from the ring connector to the load cell. In some embodiments, the cradle includes one or more guide rails configured to align a surface of the ring connector with the cradle. In some embodiments, the ring connector includes a protrusion configured to engage a recess disposed in a surface of the cradle.

Also disclosed is a method of measuring a fluid flow including, providing a ring connector configured to be coupled to a fluid collection system and including a first electrical contact disposed on a first surface and a load cell including a second electrical contact disposed on a second surface, urging the ring connector along a first axis until the first surface of the ring connector engages the second surface of the load cell, releasably securing the ring connector to the load cell, transferring a force from the fluid collection system to the ring connector to the load cell, and determining a fluid flow by determining a change in force over time.

In some embodiments, the force is transferred from the ring connector to the load cell along a second axis extending perpendicular to the first axis. In some embodiments, releasably securing the ring connector to the load cell includes rotating a latch that is hingedly coupled to the ring connector, the latch engaging a flange extending from the load cell in a snap-fit engagement. In some embodiments, the ring connector includes a protrusion extending from a surface and configured to engage a recess disposed on the load cell to secure the ring connector thereto. In some embodiments, the method further includes an O-ring disposed between the ring connector and the load cell and encircling one of the first electrical contact or the second electrical contact. In some embodiments, releasably securing the ring connector to the load cell includes actuating an actuator to release a first locking arm and a second locking arm, and allowing a biasing member to transition the first locking arm and the second locking arm from the unlocked position to the locked position.

In some embodiments, the first locking arm and the second locking arm are slidably engaged with the load cell along a second axis extending perpendicular to the first axis. In some embodiments, the method further includes actuating a release arm to transition the first locking arm and the second locking arm from the locked position to the unlocked position. In some embodiments, releasably securing the ring connector to the load cell includes a spring clip transition between a locked position and an unlocked position to engage a surface of a cradle dispose on the load cell. In some embodiments, the cradle includes a seat configured to support a bottom surface of the ring connector and transfer a force from the ring connector to the load cell.

BRIEF DESCRIPTION OF THE DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DETAILED DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Terminology

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Singular forms of "a," "an," and "the" include plural references unless the context clearly dictates otherwise.

In the following description, certain terminology is used to describe aspects of the invention. For example, in certain situations, the term "logic" is representative of hardware, firmware or software that is configured to perform one or more functions. As hardware, logic may include circuitry having data processing or storage functionality. Examples of such circuitry may include, but are not limited or restricted to a hardware processor (e.g., microprocessor with one or more processor cores, a digital signal processor, a programmable gate array, a microcontroller, an application specific integrated circuit "ASIC," etc.), a semiconductor memory, or combinatorial elements.

Alternatively, logic may be software, such as executable code in the form of an executable application, an Application Programming Interface (API), a subroutine, a function, a procedure, an applet, a servlet, a routine, source code, object code, a shared library/dynamic load library, or one or more instructions. The software may be stored in any type of a suitable non-transitory storage medium, or transitory storage medium (e.g., electrical, optical, acoustical or other form of propagated signals such as carrier waves, infrared signals, or digital signals). Examples of non-transitory storage medium may include, but are not limited or restricted to a programmable circuit; semiconductor memory; non-persistent storage such as volatile memory (e.g., any type of random access memory "RAM"); or persistent storage such as non-volatile memory (e.g., read-only memory "ROM," power-backed RAM, flash memory, phase-change memory, etc.), a solid-state drive, hard disk drive, an optical disc drive, or a portable memory device. As firmware, the executable code may be stored in persistent storage.

The term "computing device" should be construed as electronics with the data processing capability and/or a capability of connecting to any type of network, such as a public network (e.g., Internet), a private network (e.g., a wireless data telecommunication network, a local area network "LAN", etc.), or a combination of networks. Examples of a computing device may include, but are not limited or restricted to, the following: a server, an endpoint device (e.g., a laptop, a smartphone, a tablet, a "wearable" device such as a smart watch, augmented or virtual reality viewer, or the like, a desktop computer, a netbook, a medical device, or any general-purpose or special-purpose, user-controlled electronic device), a mainframe, internet server, a router; or the like.

A "message" generally refers to information transmitted in one or more electrical signals that collectively represent electrically stored data in a prescribed format. Each message may be in the form of one or more packets, frames, HTTP-based transmissions, or any other series of bits having the prescribed format.

The term "computerized" generally represents that any corresponding operations are conducted by hardware in combination with software and/or firmware.

Figure 1A:
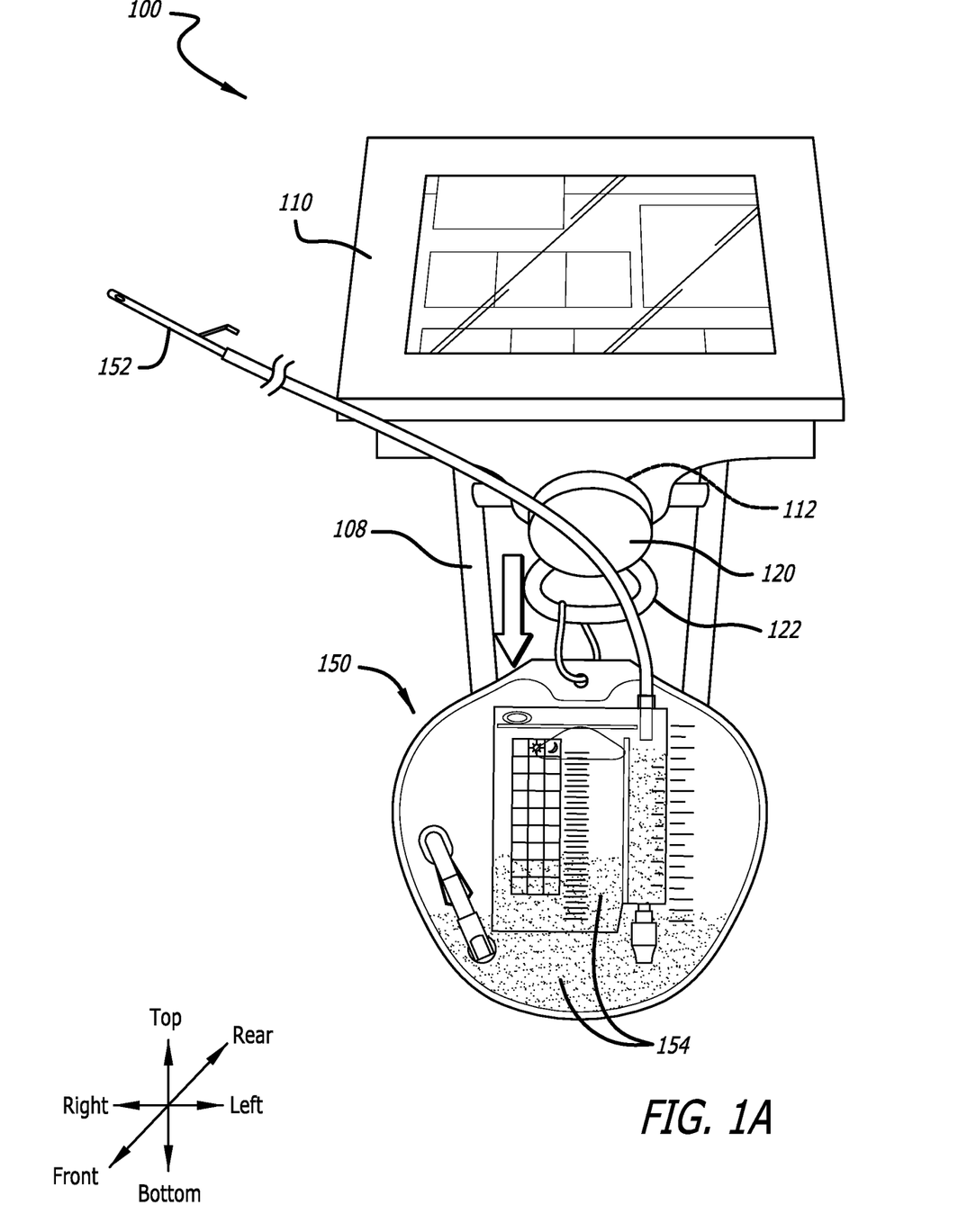
FIG. 1A shows a perspective view of an exemplary automatic fluid flow system including a fluid collection system, in accordance with embodiments disclosed herein.

Labels such as "left," "right," "upper", "lower," "top," "bottom," "front," "back," and the like are used for convenience and are not intended to imply, for example, any particular fixed location, orientation, or direction. Instead, such labels are used to reflect, for example, relative location, orientation, or directions. To assist in the description of embodiments described herein, the "top," "bottom," "left," "right," "front" and "back" directions are in reference to the orientation of the device as shown in FIG. 1A. A vertical axis extends between a top direction and a bottom direction. A lateral axis extends horizontally between a left direction and a right direction, substantially normal to the vertical axis. A transverse axis extends horizontally between a front direction and a back direction, substantially normal to both the vertical and lateral axes. A horizontal plane is defined by the lateral and transverse axes. A median plane is defined by the vertical and transverse axes. A frontal plane is defined by the vertical and lateral axes.

Unless defined otherwise, all technical and scientific terms used herein have the same meaning as commonly understood by those of ordinary skill in the art.

Figure 1B:
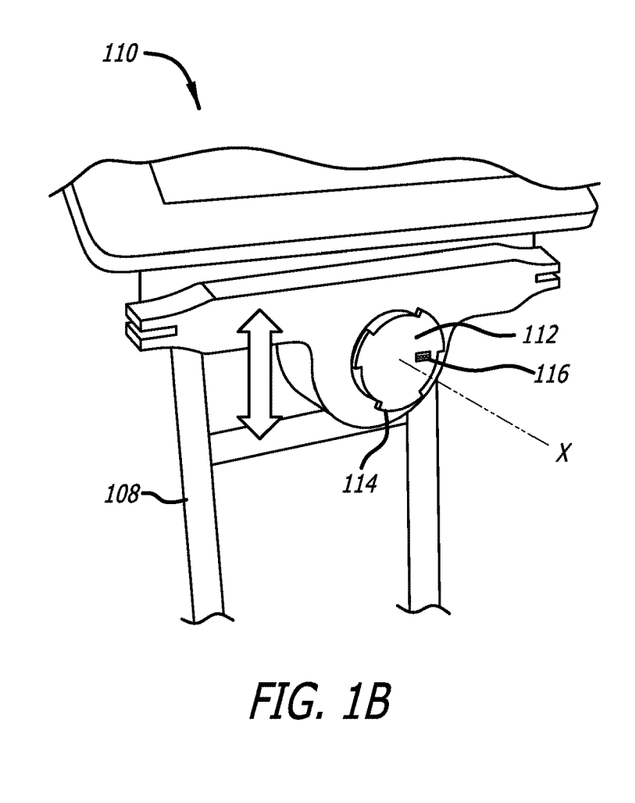
FIGS. 1B-1C show perspective views of a load cell interface and a ring connector of an exemplary automatic fluid flow system, in accordance with embodiments disclosed herein.
Figure 1C:
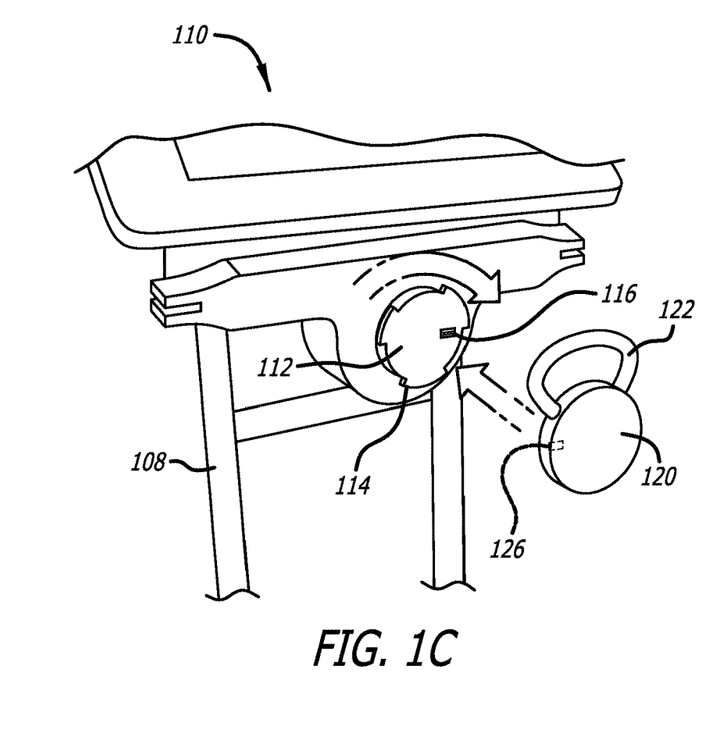

FIGS. 1A-1C show details of an exemplary automatic fluid flow measuring system ("system") 100 including a fluid collection system 150 coupled thereto, in accordance with embodiments disclosed herein. The automatic fluid flow system 100 generally includes a console 110 including a load cell interface ("load cell") 112 configured to engage a ring connector ("ring") 120. The ring connector 120 can include a loop 122, peg, hook, or similar structure from which a fluid collection system 150 can be suspended. The fluid collection system 150 can generally include one or more collection containers 154 in fluid communication with a catheter 152 or similar device configured to drain a fluid from a cavity of a patient. Optionally, the console 110 can be supported by a stand 108, or similar structure configured to support the console 110, ring 120, fluid collection system 150, and the like.

In an embodiment, the catheter 152 can be an internal catheter or an external catheter. Exemplary catheters can include external urinary catheter, internal urinary catheter, Foley catheter, balloon catheter, peritoneal catheters, or the like. Exemplary fluids collected can include urine, blood, peritoneal fluid, interstitial fluid, or the like. In an embodiment, the catheter 152 can be a Foley catheter configured to drain a fluid, e.g. urine, from a bladder of a patient.

As shown in FIG. 1B, the load cell interface 112 can be configured to detect a change in vertical movement relative to the console 110. In an embodiment, the load cell interface 112 can be configured to detect a force applied thereto, along an axis extending parallel to a front surface of the load cell 112, or perpendicular to a central transverse axis (x) of the load cell. For example, as shown in FIG. 1C, a ring connector 120 can be coupled to the load cell interface 112 by engaging the load cell 112 along the central transverse axis (x). The ring connector 120 can then be locked to the load cell 112 by rotating the ring connector 120 about the central transverse axis (x). In an embodiment, the ring connector 120 can be rotated between 5° and 360°. In an embodiment, the ring connector 120 can be rotated substantially 180°. A fluid collection system 150 can then be coupled to the loop 122 of the ring connector 120. A change in fluid volume within the fluid collection system 150, and thereby a change in weight thereof, causes a change in force applied to the load cell interface 112. The change in force can be substantially along a vertical axis, however it will be appreciated that the load cell interface 112 can detect force changes along other axes in three-dimensional space, as well.

The change in force applied to the load cell interface 112 can be detected by the console 110 to determine a change in fluid volume within the fluid collection system 150. This information can then be stored, analyzed, displayed, or communicated to one or more external computing devices or networks, e.g. an Electronic Health Record (EHR) system, network, or the like.

In an embodiment, the load cell interface 112 can include an engagement structure such as a locking mechanism 114, and an electrical contact interface 116. The locking mechanism 114 can be configured to engage a corresponding locking mechanism disposed on the ring connector 120 to secure the ring connector 120 to the load cell interface 112, as described in more detail herein. As noted, the locking mechanism 114 can be a rotational locking mechanism 114 where the ring connector 120 is rotated through a frontal plane by substantially 180° to transition the ring connector between a locked configuration (FIG. 1A) and an unlocked configuration (FIG. 1C).

In an embodiment, the electrical contact interface 116 can be configured to engage a corresponding electrical contact interface 126 disposed on the ring connector 120 to communicatively couple the ring connector 120 to the load cell interface 112 of the console 110. In an embodiment, the ring connector electrical contact interface 126 engages the load cell electrical contact interface 116 in one of the locked configuration or the unlocked configuration.

In an embodiment, the ring connector 120 can include one or more processors, memory, storage logic, communication logic, or the like, configured to store information and communicate with the console 110 by way of the ring connector electrical contact interface 126 and the load cell electrical contact interface 116. For example, the ring connector 120 can store fluid flow information, system information, patient information, or the like. Fluid flow information can include current or historical fluid volume information, fluid flow information (i.e. change in volume over time), combinations thereof or the like. System information can include the make, model, serial number, etc. of the ring connector 120, fluid collection system 150, the console 110, components thereof, or the like. Patient information can include height, weight, blood pressure, etc. of the patient, or similar health record information.

Advantageously, the fluid flow information, system information, patient information, and the like, can be stored to the ring connector 120 and transported with the collection system 150 and the patient. The ring connector 120 and collection system 150 assembly can then be coupled to a different console 110, e.g. during transport or console malfunction, and continue to measure fluid flow without losing the historical data, or transferring the data separately. As such, the data remains with the patient and the collection system and is not lost.

FIGS. 2A-2D show embodiments of a load cell interface 212 and a ring connector 220 including an engagement structure having a latch locking mechanism 214 configured to releasably engage the ring connector 220 with the load cell 212. The ring connector 220 can define a front surface, a rear surface and a side surface extending therebetween. The load cell 212 can define a front surface, a rear surface and a side surface extending therebetween. To note, while one of the load cell 212 or the ring connector 220 can define a circular shaped front surface or rear surface, it will be appreciated that other closed curve, regular or irregular polygonal shapes are also contemplated including triangular, square, hexagonal, or the like.

Figure 2A:
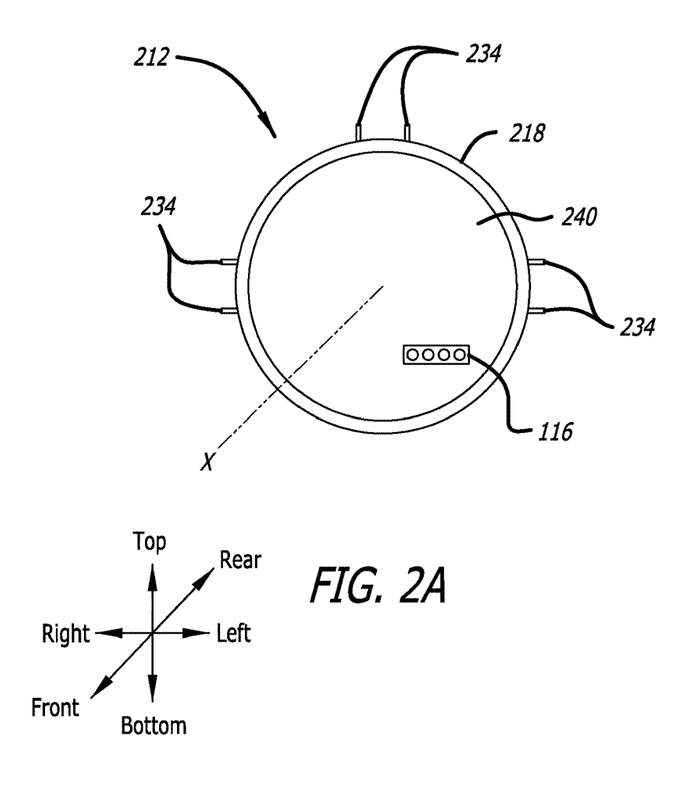
FIG. 2A shows a front view of a load cell interface, in accordance with embodiments disclosed herein.
Figure 2B:
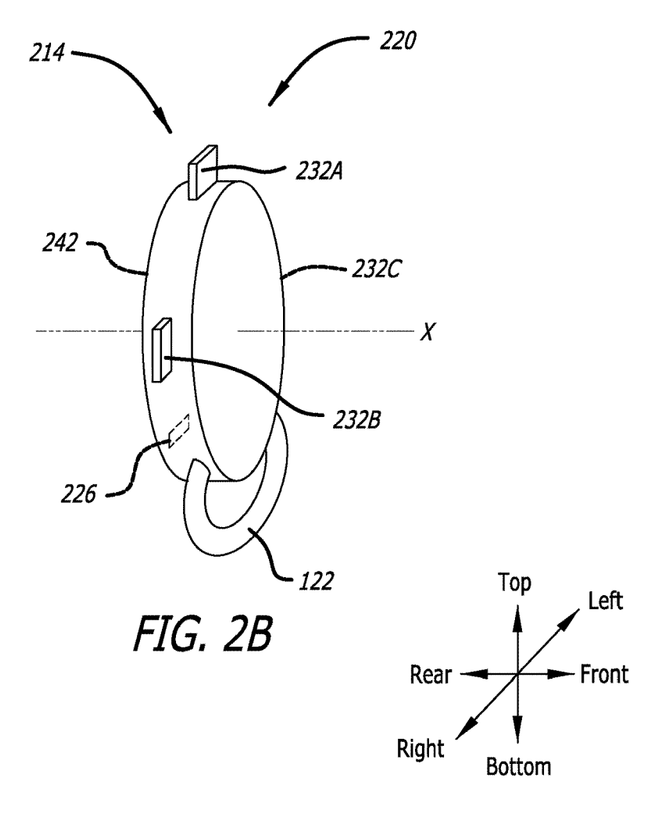
FIG. 2B shows a perspective side view of a ring connector, in accordance with embodiments disclosed herein.

In an embodiment, the load cell 212 can include a flange 218 extending radially therefrom, i.e. extending substantially parallel to a front surface of the load cell 212. In an embodiment, the flange 218 can extend along a portion of a side surface of the load cell 212. In an embodiment, the flange 218 can extend annularly about the load cell 212. In an embodiment, the latch locking mechanism 214 includes one or more latches 232 hingedly coupled with the ring connector 220 and configured to releasably engage a portion of flange 218. In an embodiment, the latch 232 rotates and engages the flange 218 in an interference fit, press-fit, snap-fit engagement, or the like.

Figure 2C:
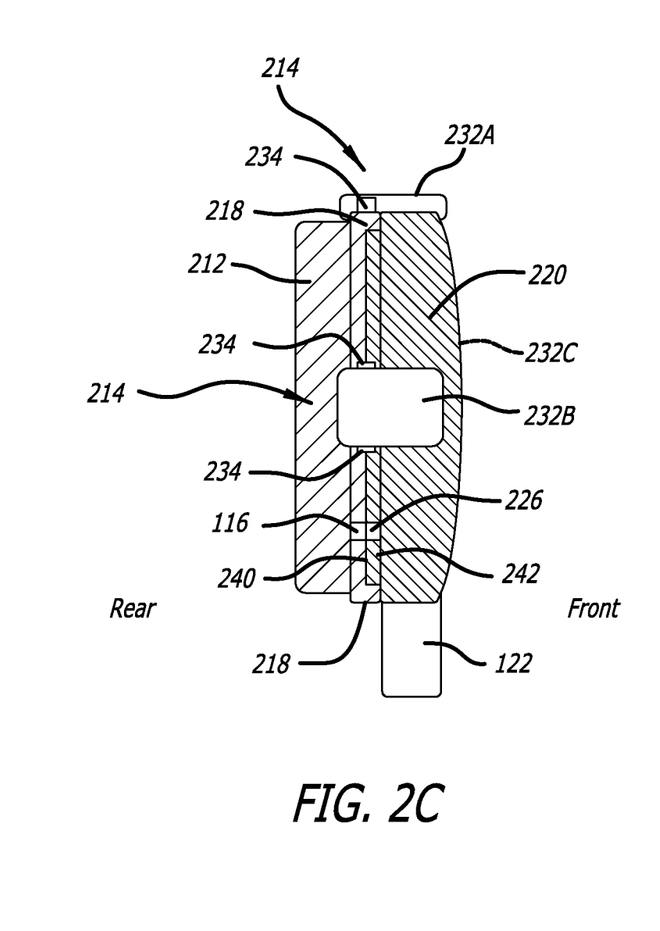
FIG. 2C shows a side view of a ring connector and a load cell interface in a locked position, in accordance with embodiments disclosed herein.
Figure 2D:
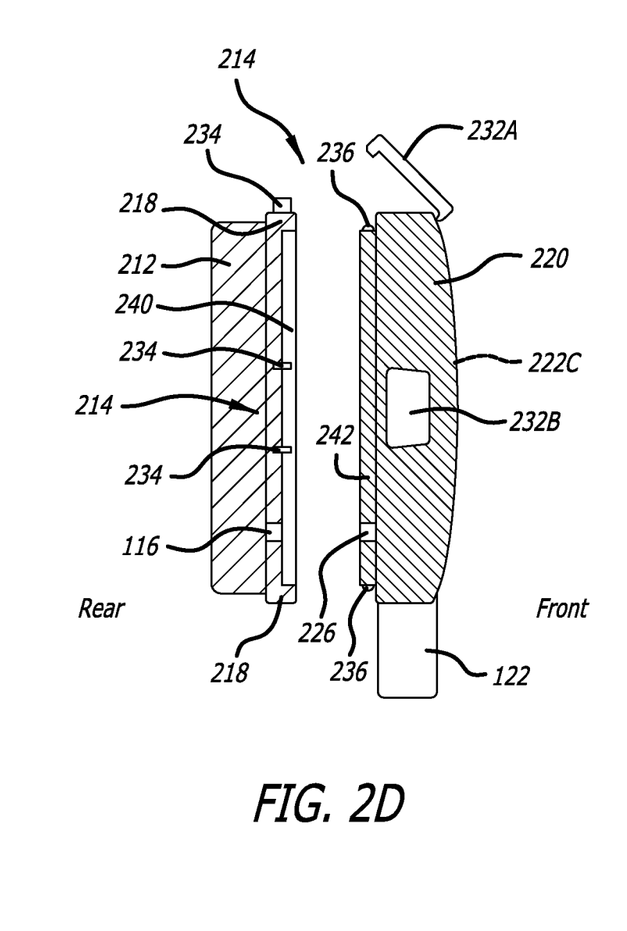
FIG. 2D shows a side view of a ring connector and a load cell interface in an unlocked position, in accordance with embodiments disclosed herein.

In an embodiment, one or more of the latches 232 can be hingedly coupled to one of the front surface, side surface, or rear surface of the one of the ring connector 220, or combinations thereof. In an embodiment the latches 232 can be coupled to the same surface or different surfaces. For example, as shown, the ring connector 220 can include a top latch 232A, a left latch 232B, and a right latch 232C, each coupled to a side surface of the ring connector 220. However, it will be appreciated that any number, orientation (e.g. hingedly coupled to either the load cell 212 or the ring connector 220), or configuration of latches 232 are considered to fall within the scope of the present invention. As shown in FIGS. 2C-2D, the one or more latches 232 can be rotated to engage the flange 218 and secure the ring connector 220 to the load cell 212. Advantageously, the one or more latches 232 can be hingedly coupled to and releasably engage, a side surface of one of the ring connector 220 or the load cell 212 to provide minimal obstruction between the rear surface of the ring connector 220 and a front surface of the load cell 212. This can provide a quick and intuitive engagement between the ring connector 220 and the load cell 212, expediting the coupling process and mitigating failure of the locking engagement.

In an embodiment, a front surface of the load cell 212 can include a recess 240 configured to receive a protrusion 242 extending from a rear surface of the ring connector 220. The protrusion 242 can engage the recess 240 to facilitate alignment of the ring connector 220 with the load cell 212. Further, the protrusion 242 can engage the recess 240 to transfer a force from the ring connector 220, and the fluid collection system 150 coupled thereto, to the load cell 212. For example, as a fluid volume within the fluid collection system 150 increases, the weight of the fluid collection system 150 also increases and applies a downward force on the loop 122 and ring connector 220. The protrusion 242 engages the recess 240 and transfers the downward force to the load cell 212 which in turn is detected by the console 110. The console 110 can then determine an amount of fluid disposed within the fluid collection system 150 by a corresponding change in movement or pressure applied to the load cell 212. Similarly, the console 110 can determine a fluid flow by determining a change in fluid volume over time. As will be appreciated, the ring connector 220 can include any number, shape, or configuration of protrusions 242. Similarly, the load cell 212 can include any number, shape, or configuration of recesses 240. Further, one of the load cell 212 or the ring connector 220 can include a recess 240, protrusion 242, or combinations thereof.

In an exemplary method of use, a load cell 212 and a ring connector 220 including a latch locking mechanism 214 is provided, as described herein. A rear surface of the ring connector 220 can be aligned with a front surface of the load cell 212. In an embodiment, a protrusion 242 extending from one of the ring connector 220 or the load cell 212 can align and engage with a recess 240 disposed on one of the load cell 212 or the ring connector 220. The protrusion 242 can facilitate alignment and securement of the ring connector 220 with the load cell 212. The rear surface of the ring connector 220 can engage the front surface of the load cell 212. A latch 232 can be rotated from an unlocked configuration to engage a flange 218 in a locked configuration.

In an embodiment, the load cell 212 can include an electrical contact 116 disposed on a front surface thereof. The ring connector 220 can include an electrical contact 226 disposed on a rear surface and configured to align with the load cell electrical contact 116. In the locked configuration, the ring connector electrical contact 226 contacts the load cell electrical contact 116 to communicatively couple with ring connector 220 with the console 110, as described herein. Advantageously, the ring connector electrical contact 226 engages the load cell electrical contact 116 along a transverse axis that extends perpendicular to the surfaces that the electrical contacts 116, 226 are disposed on. This mitigates wear on the electrical contact surfaces and provides a reliable communicative coupling therebetween, extending the usable life of the system 100.

In an embodiment, the flange 218 can include one or more guide plates 234 extending normal to the flange 218. The guide plates 234 can be disposed adjacent the latch 232, and can receive the latch 232 therebetween when the latch 232 is in the locked configuration. In an embodiment, the guide plates 234 can contact the latch 232 when the latch 232 is in the locked configuration. The guide plates 234 can be configured to guide the latch 232 to the locked position on the load cell 212. The guide plates 234 can support the latch 232 to inhibit movement of the latch 232, for example, movement perpendicular to the axis of rotation of the latch 232. Advantageously, the guide plates 234 provide an intuitive receiving position for the latch 232 to align the latch 232, and thereby the ring connector 220, with the load cell 212.

In an embodiment, one of the ring connector 220 or the load cell 212 can include an O-ring 236 or similar grommet extending annularly along an edge of the ring connector and configured to encircle the electrical contacts 116, 226 when in the locked position. As shown, the O-ring 236 extends along a side surface of the protrusion 242 and can engage a side surface of the recess 240 on the load cell 312 when in the locked configuration. However, it will be appreciated that the O-ring 236 can extend along a portion of the rear surface of the ring connector 220, a rear surface of the protrusion 242, a front surface of the load cell 312, an inner surface of the recess 240, combinations thereof or the like. Advantageously, the O-ring 236 can engage the ring connector 220 and the load cell 212 in the locked position and provide a fluid-tight seal therebetween. This prevents any fluid from accessing the electrical contacts 116, 226, and causing a short-circuit, or similar damage to the system 100. Further, the O-ring 236 can provide an interference fit between the ring connector 220 and the load cell 212 further securing the ring connector 220 thereto.

Advantageously, the ring connector 220 can engage the load cell 212 along a transverse axis, which is parallel to an axis of connection between the load cell 212 and the console 110. Worded differently, the ring connector 220 engages the load cell 212 along an axis with which the load cell 212 is most supported and thereby mitigates damage to the load cell 212 relative to other directions of engagement, e.g. rotational about the transverse axis, termed "off-axis." Further, the latches 232 provide an intuitive locking mechanism 214.

FIGS. 3A-3D show an embodiment of a load cell 312 and a ring connector 320 including an engagement structure having a spring latch locking mechanism 314 configured to releasably secure the ring connector 320 with the load cell 312. The ring connector 320 can define a front surface, a rear surface and a side surface extending therebetween. The load cell 312 can define a front surface, a rear surface and a side surface extending therebetween. To note, while one of the load cell 312 or the ring connector 320 can define a substantially circular shaped front surface or rear surface, it will be appreciated that other closed curve, regular or irregular polygonal shapes are also contemplated including triangular, square, hexagonal, or the like.

Figure 3A:
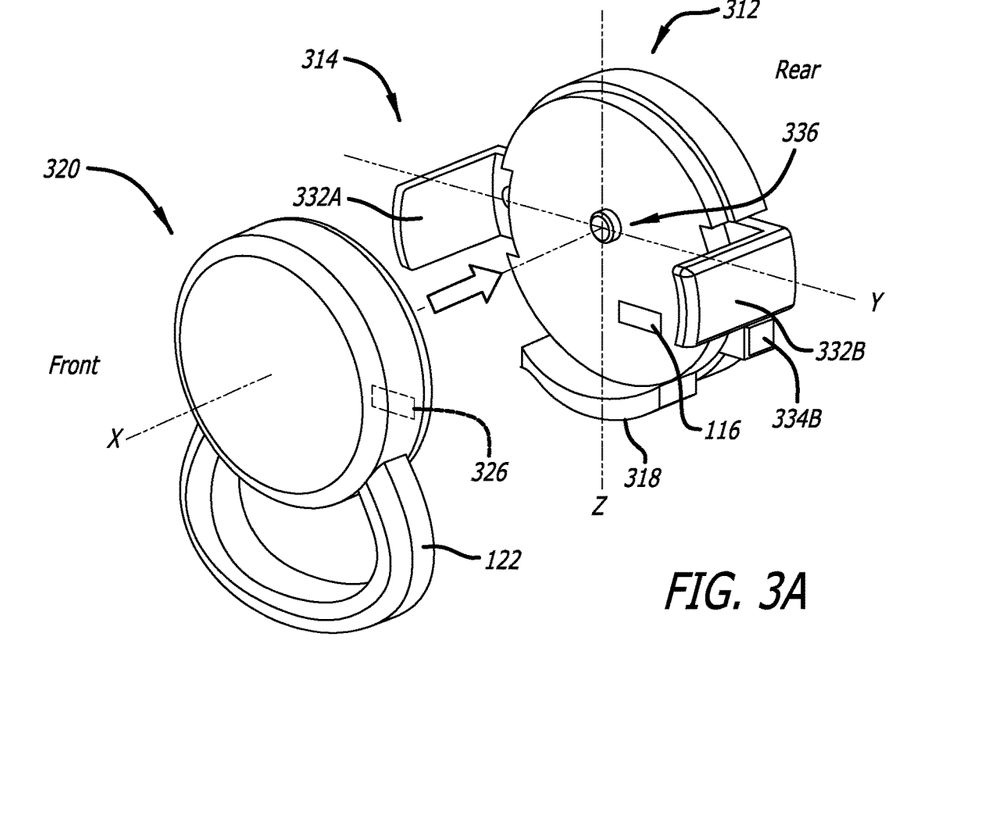
FIG. 3A shows a perspective view of a ring connector and a load cell interface in an unlocked position, in accordance with embodiments disclosed herein.
Figure 3B:
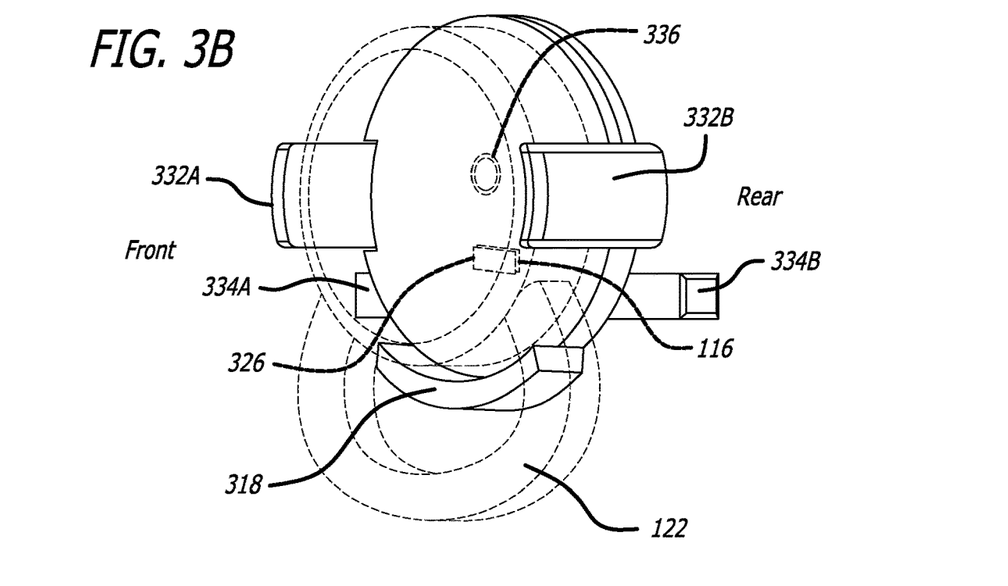
FIG. 3B shows a perspective view of a ring connector and a load cell interface in a locked position, in accordance with embodiments disclosed herein.

In an embodiment, the spring latch locking mechanism 314 includes one or more locking arms 332, e.g. a left locking arm 332A and a right locking arm 332B disposed opposite the left locking arm 332A across a central transverse axis (x). It will be appreciated that other combinations and orientations of locking arms 332 are also contemplated to fall within the scope of the present invention. The locking arms 332A, 332B can be slidably engaged with the load cell 312 along an axis extending perpendicular to a transverse axis, for example a lateral axis (y).

The load cell 312 can further include a seat 318 extending from a lower edge of the load cell 312 and configured to engage a lower surface of the ring connector 320 in the locked configuration (FIG. 3B). Advantageously, the seat 318 can be configured to support the weight of the ring connector 320, and optionally the fluid collection system 150 coupled thereto, and transfer a downward force from the ring connector 320 to the load cell 312.

The load cell 312 can include an actuator 336 disposed on a front surface of the load cell 312. As shown the actuator 312 can be disposed substantially at a center point on the front surface of the load cell 312. However, it will be appreciated that the actuator 336 can be disposed in other configurations or on other surfaces of the load cell 312, e.g. a top surface of the seat 318, or the like.

In an embodiment, the actuator 336 can include a push button configured to be actuated by the ring connector 320 when the ring connector 320 engages the load cell 312. However, it will be appreciated that the actuator 336 can include various types of actuators employing various modalities without departing from the spirit of the invention. Exemplary actuators can include pressure transducers, optical transducers, magnetic switches, electro-magnetic actuators, solenoids, radio-frequency tags, mechanical switches, combinations thereof, or the like. In an embodiment, the load cell 312 can include two or more actuators 336.

Figure 3C:
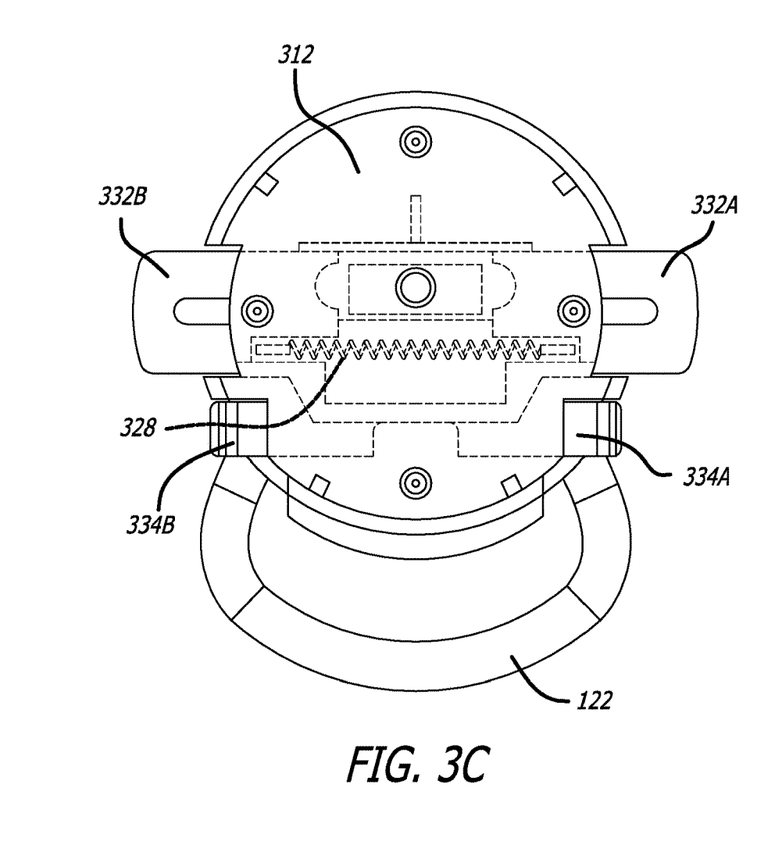
FIG. 3C shows a rear view of a load cell interface and a ring connector in an unlocked position, in accordance with embodiments disclosed herein.
Figure 3D:
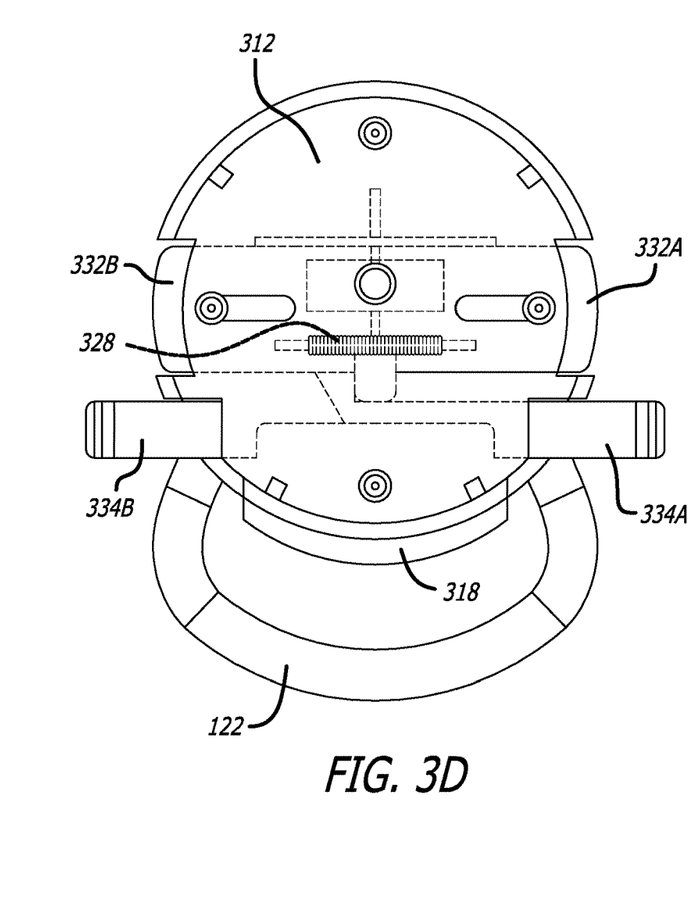
FIG. 3D shows a rear view of a load cell interface and a ring connector in a locked position, in accordance with embodiments disclosed herein.

FIGS. 3C-3D show a rear side view of the load cell 312 with the ring connector 320 engaged therewith. FIG. 3C shows the load cell 312 in the unlocked configuration. FIG. 3D shows the load cell 312 in the locked configuration. The load cell 312 can include a biasing member 328 configured to bias the locking arms 332 towards a locked configuration (FIG. 3D), i.e. in a radially inward configuration relative to the central transverse axis (x). In the unlocked configuration, the locking arms 332 can be displaced in a radially outward configuration relative to the central transverse axis (x) and can be held in the unlocked configuration by a ratchet, pawl, catch or similar suitable mechanism. Actuating the actuator 336 can release the locking arms 332 and allow the biasing member 328 to transition the locking arms 332 from the unlocked configuration (FIG. 3C) to the locked configuration (FIG. 3D).

In an embodiment, the load cell 312 can further include a release arm 334, or similar actuator, configured to transition the locking arms 332 from the locked configuration (FIG. 3D) to the unlocked configuration (FIG. 3C). In an embodiment, the load cell 312 can include a left release arm 334A and a right release arm 334B, disposed opposite the left release arm 334A across a central vertical axis (z). It will be appreciated, however, that other combinations and orientations of release arm(s) 334 are also contemplated to fall within the scope of the present invention. The release arms 334A, 334B can be slidably engaged with the load cell 312 along a lateral axis, extending perpendicular to the vertical axis. In the unlocked configuration (FIG. 3C), the release arms 334A, 334B can be disposed in a radially inward configuration relative to the central vertical axis (z). In the locked configuration (FIG. 3D), the release arms 334A, 334B can be disposed in a radially outward configuration relative to the central vertical axis (z).

In an embodiment, as the biasing member 328 transitions the locking arms 332 from the unlocked configuration (FIG. 3C) to the locked configuration, (FIG. 3D), the locking arms 332 can be configured to transition the release arms 334 from the laterally inward position (FIG. 3C) to the laterally outward position (FIG. 3D). In an embodiment, the release arms 334 can be configured such that transitioning the release arms 334 from the laterally outward position (FIG. 3D) to the laterally inward position (FIG. 3C) can transition the locking arms 332 from the locked configuration to the unlocked configuration.

In an embodiment, the load cell 312 can include an electrical contact 116 disposed on a front surface thereof. The ring connector 320 can include an electrical contact 326 disposed on a rear surface and configured to align with the load cell electrical contact 116. In the locked configuration, the ring connector electrical contact 326 engages the load cell electrical contact 116 to communicatively couple with ring connector 320 with the console 110, as described herein. Advantageously, the ring connector electrical contact 326 engages the load cell electrical contact 116 along a transverse axis that extends perpendicular to the surfaces that the electrical contacts 116, 326 are disposed on. This mitigates wear on the electrical contact surfaces and providing a reliable communicative coupling therebetween and extends the usable life of the system 100.

Figures 4A, 4B, 4D:
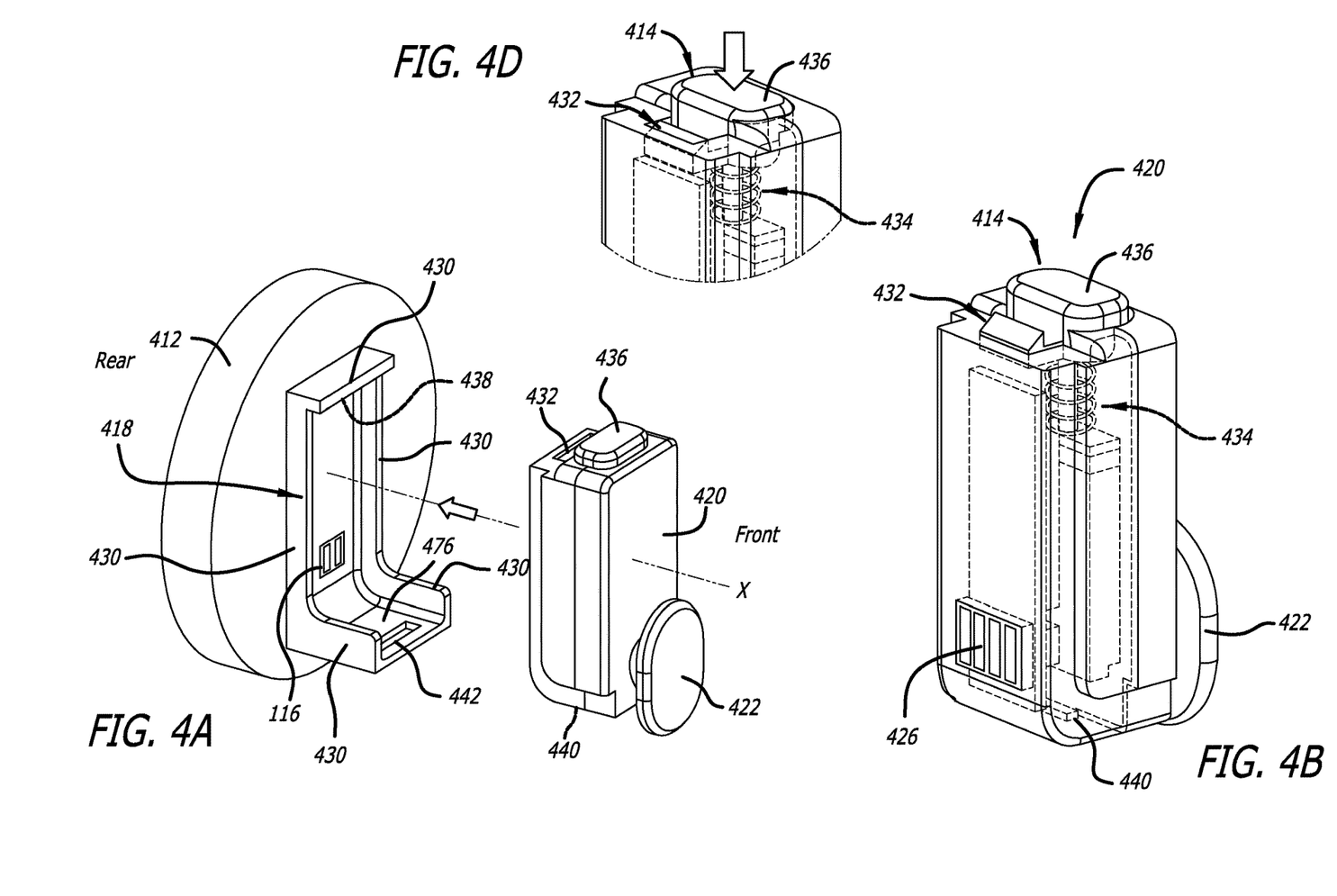
FIG. 4A shows a perspective view of a ring connector and a load cell interface in an unlocked position, in accordance with embodiments disclosed herein.
FIG. 4B shows a perspective view of a ring connector, in accordance with embodiments disclosed herein.
FIG. 4D shows close up detail of the ring connector of FIG. 4B, in accordance with embodiments disclosed herein.
Figure 4C:
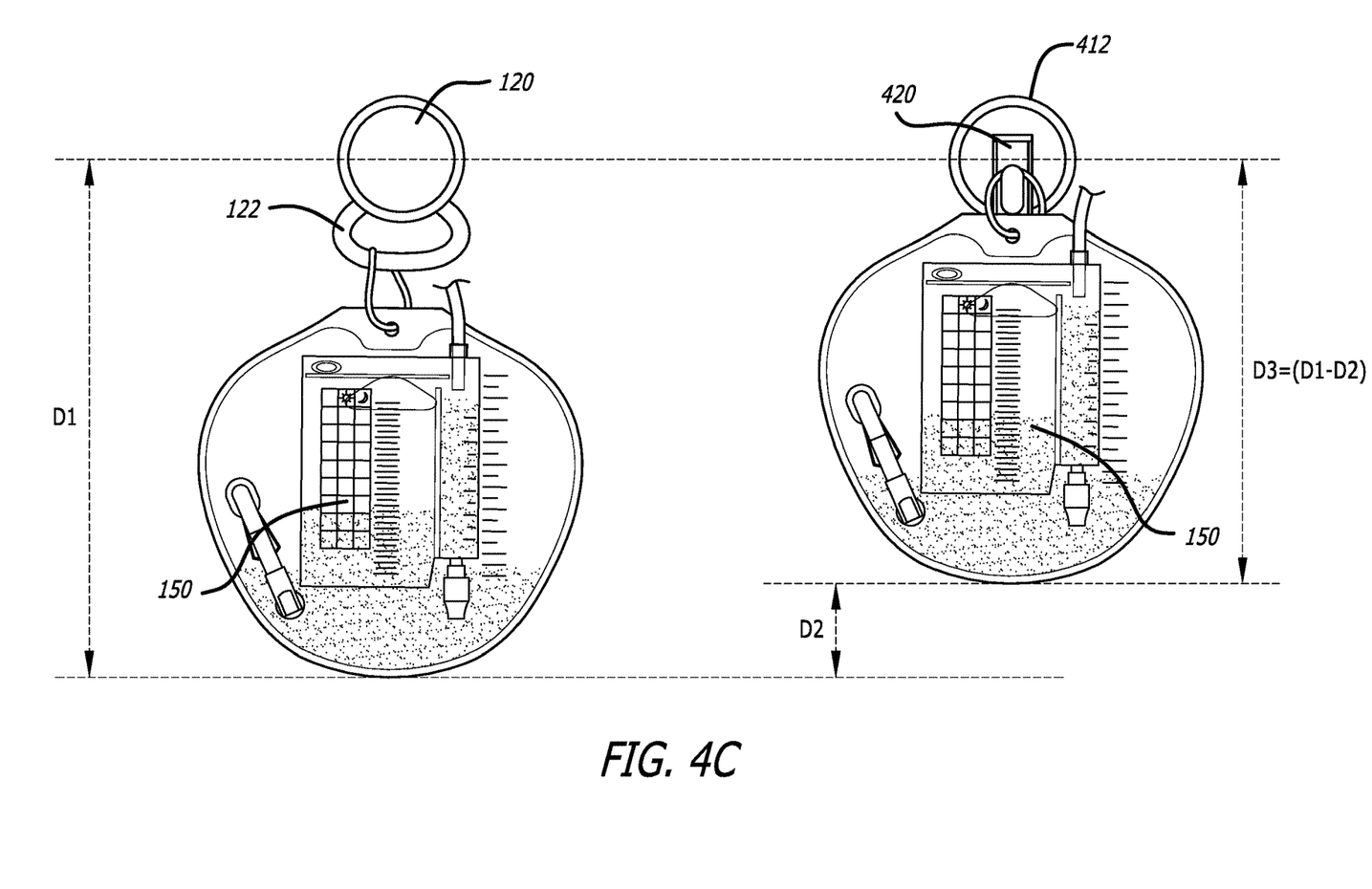
FIG. 4C shows a comparison of fluid collection system positions when suspended by different ring connector embodiments, in accordance with embodiments disclosed herein.

As shown in FIGS. 4A-4C, in an embodiment the load cell 412 and the ring connector 420 can include an engagement structure having a clip latch locking mechanism 414 configured to releasably secure the ring connector 420 with the load cell 412. In an embodiment, the ring connector 420 can define a substantially cuboid shape including a substantially rectangular front surface, a rectangular rear surface and one or more side surfaces extending therebetween. It will be appreciated, however, that the ring connector 420 can define various polygonal shapes without limitation.

The ring connector 420 can include a peg 422 extending from a surface thereof, e.g. a front surface, and configured to secure a fluid collection system 150 thereto. As shown in FIG. 4C, the peg 422 can couple the fluid collection system 150 to the ring connector 420 at a higher vertical position (e.g. vertical position D3), relative to the ring loop 122 that extend from a lower surface of a ring connector 120 (e.g. vertical position D1). The difference between the ring loop 122 vertical position (D1) and the peg 422 vertical position (D3) can be a distance D2. Advantageously, this raises the fluid collection system 150 relative to the console 110 by a distance (D2) mitigating contact with a floor surface and providing a shorter, more compact overall profile to the system 100. As will be appreciated, the peg 422 can include a loop, hook, or similar structure configured to couple the fluid collection system to the ring connector 420. In an embodiment, the peg 422 can be disposed proximate a bottom surface of the ring connector 420, proximate a top surface of the ring connector 420, or disposed at any vertical position along the front surface of the ring connector 420. In an embodiment, the peg 422 can be disposed at any vertical position along a side surface of the ring connector 420. In an embodiment, the peg 422 can be disposed on a top surface of the ring connector 420. In an embodiment the peg 422 can extend from the ring connector 420 horizontally, vertically, or at an angle therebetween.

As shown in FIGS. 4A-4B, in an embodiment, the load cell 412 can include a cradle 418 configured to engage a surface of the ring connector 420. For example, the cradle 418 can be configured to receive a portion of a rear surface, a side surface, or a bottom surface of the ring connector 420, or combinations thereof. In an embodiment, the cradle 418 can includes a seat 476 extending horizontally from the front surface of the load cell 412. The seat 476 can be configured to engage a bottom surface of the ring connector 420, when the ring connector 420 is engaged with the load cell 412. Advantageously, the seat 476 can be configured to support the weight of the ring connector 420, and optionally the fluid collection system 150 coupled thereto, and transfer any downward force from the ring connector 320 to the load cell 312. In an embodiment, the cradle 418 can include one or more guide rails 430 extending along an edge of the cradle 418 and configured to align the ring connector 420 with the cradle 418. Advantageously, the cradle 418 and guide rail 430 provides an intuitive system to align the ring connector 420 with the load cell 412.

In an embodiment, the clip latch locking mechanism 414 can include one or more spring clips 432 disposed on the ring connector 420. The spring clip 432 can be configured to engage the cradle 418 to releasably secure the ring connector 420 to the load cell 412. The spring clip 432 can be slidably engaged with the ring connector 420 between a locked position (FIG. 4B) and an unlocked position (FIG. 4D). The spring clip 432 can include a biasing member 434, e.g. a compression spring, configured to bias the spring clip 432 towards the locked position. The spring clip 432 can further include an actuator 436 configured to transition the spring clip 432 from the locked position to the unlocked position.

In an embodiment, the cradle 418 can include a recess 438 configured to receive the spring clip 432 and releasably secure the ring connector 420 to the cradle 418. One of the spring clip 432 or the recess 438 can include a chamfered edge to facilitate engagement of the spring clip 432 with the cradle recess 438. In an embodiment, the ring connector 420 can include a first spring clip 432 disposed proximate a top surface of the ring connector 420 and configured to engage a recess 438 disposed on an underside of a top surface of the cradle 418. However, it will be appreciated that the clip latch locking mechanism 414 can include one or more spring clips 432 disposed proximate a top surface, bottom surface, side surface, or combinations thereof.

In an embodiment, the ring connector 420 can include a protrusion 440 extending from a surface of the ring connector 420 and configured to engage a recess 442, aperture, detent, or similar structure disposed in the cradle 418. The protrusion 440 and recess 442 can be configured to further secure the ring connector 420 with the load cell 412. As shown, the protrusion 440 extends from a bottom surface of the ring connector 420 and is configured to engage a recess 442 disposed in the seat 476 of the cradle 418. The protrusion 440 and recess 442 can be disposed opposite a spring clip 432. However, it will be appreciated that one or more protrusions 440 and recesses 442 can be disposed proximate a top surface, bottom surface, side surface of the ring connector 420 or combinations thereof.

In an embodiment, the load cell 412 can include an electrical contact 116 disposed on a front surface thereof. The ring connector 420 can include an electrical contact 426 disposed on a rear surface and configured to align with the load cell electrical contact 116. In the locked configuration, the ring connector electrical contact 426 engages the load cell electrical contact 116 to communicatively couple with ring connector 420 with the console 110, as described herein. Advantageously, the ring connector electrical contact 426 engages the load cell electrical contact 116 along a transverse axis that extends perpendicular to the surfaces that the electrical contacts 116, 426 are disposed on. This mitigates wear on the electrical contact surfaces and provides a reliable communicative coupling therebetween, extending the usable life of the system 100.

In an exemplary method of use a user can actuate the actuator 436 to overcome the force of the biasing member 434 and transition the spring clip 432 from the locked position to the unlocked position. In an embodiment, the ring connector 420 can engage the load cell 412 along a transverse axis until a surface of the ring connector 420 engages the cradle 418 disposed on the load cell 412. In an embodiment, a protrusion 440 extending from a lower surface engages a first recess 442 disposed in a seat 476 of the cradle 418 to inhibit movement between a lower surface of the ring connector 420 and the seat 476. A user can then release the actuator 436 to allow the biasing member 434 to transition the spring clip 432 from the unlocked position to the locked position where the spring clip 422 engages a second recess 438 disposed in the cradle 418 opposite the first recess 442. A user can then couple a fluid collection system 150 with a peg 422, or similar structure, extending from a surface of the ring connector 420, e.g. a front surface. Optionally, a user can couple the fluid collection system 150 with the peg 422 prior to engaging the ring connector 420 with the load cell 412.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. An automatic fluid flow measuring system, comprising:
    a ring connector configured to be coupled to a fluid collection system and including a first electrical contact disposed on a first surface;
    a load cell including a second electrical contact disposed on a second surface, the load cell configured to engage and retain the ring connector such that the first electrical contact engages the second electrical contact along a first axis extending perpendicular to both the first surface and the second surface; and
    an engagement structure engaging a side surface of one of the ring connector or the load cell and configured to releasably secure the ring connector to the load cell.

2. The automatic fluid flow measuring system according to claim 1, wherein the engagement structure includes a latch hingedly coupled to one of the ring connector or the load cell and rotatable between an unlocked position and a locked position, the latch engaging a flange in the locked position to releasably secure the ring connector to the load cell.

3. The automatic fluid flow measuring system according to claim 2, wherein the latch engages the flange in one of an interference fit, a press-fit, or a snap-fit engagement.

4. The automatic fluid flow measuring system according to claim 2, wherein the flange extends along a portion of the side surface of the load cell and extends parallel to the second surface of the load cell.

5. The automatic fluid flow measuring system according to claim 2, wherein the ring connector includes a protrusion, extending from a rear surface thereof, and wherein the load cell includes a recess disposed on a front surface thereof and configured to receive the protrusion.

6. The automatic fluid flow measuring system according to claim 2, wherein the load cell includes a pair of guide plates extending from the side surface of one of the load cell or the ring connector and configured to receive the latch therebetween.

7. The automatic fluid flow measuring system according to claim 2, further including an O-ring configured to engage both the ring connector and the load cell in the locked position to provide a fluid-tight seal therebetween.

8. The automatic fluid flow measuring system according to claim 7, wherein the O-ring extends annularly around one of a ring connector electrical contact or a load cell electrical contact.

9. The automatic fluid flow measuring system according to claim 1, wherein the engagement structure includes a first locking arm and a second locking arm slidably engaged with the load cell and transitionable between a locked position and an unlocked position.

10. The automatic fluid flow measuring system according to claim 9, wherein the first locking arm and the second locking arm are slidable along a second axis extending parallel to the second surface.

11. The automatic fluid flow measuring system according to claim 9, further including a biasing member configured to bias the first locking arm and the second locking arm to the locked position.

12. The automatic fluid flow measuring system according to claim 11, further including an actuator configured to release the first locking arm and the second locking arm and allow the biasing member to transition the first locking arm and the second locking arm from the unlocked position to the locked position.

13. The automatic fluid flow measuring system according to claim 12, wherein the actuator is disposed on the second surface and configured to be actuated by the first surface engaging the second surface.

14. The automatic fluid flow measuring system according to claim 12, wherein the actuator includes one of a push button, a pressure transducer, an optical transducer, a magnetic switch, an electro-magnetic actuator, a solenoid, or a radio-frequency tag.

15. The automatic fluid flow measuring system according to claim 9, further including a first release arm and a second release arm slidably engaged with the load cell and configured to transition the first locking arm and the second locking arm from the locked position to the unlocked position.

16. The automatic fluid flow measuring system according to claim 9, further including a seat extending from a lower surface of the load cell and configured to support a bottom surface of the ring connector to transfer a downward force from the ring connector to the load cell.

17. A method of measuring a fluid flow, comprising:
    providing a ring connector configured to be coupled to a fluid collection system and including a first electrical contact disposed on a first surface and a load cell including a second electrical contact disposed on a second surface;
    urging the ring connector along a first axis extending perpendicular to both the first surface and the second surface until the first electrical contact of the ring connector engages the second electrical contact of the load cell;
    releasably securing the ring connector to the load cell;
    transferring a force from the fluid collection system to the ring connector to the load cell; and
    determining the fluid flow by determining a change in force over time.

18. The method according to claim 17, wherein the force is transferred from the ring connector to the load cell along a second axis extending perpendicular to the first axis.

19. The method according to claim 17, wherein releasably securing the ring connector to the load cell includes rotating a latch that is hingedly coupled to the ring connector, the latch engaging a flange extending from the load cell in a snap-fit engagement.

20. The method according to claim 17, wherein the ring connector includes a protrusion extending from a surface and configured to engage a recess disposed on the load cell to secure the ring connector thereto.

21. The method according to claim 17, further including an O-ring disposed between the ring connector and the load cell and encircling one of the first electrical contact or the second electrical contact.

22. The method according to claim 17, wherein releasably securing the ring connector to the load cell includes actuating an actuator to release a first locking arm and a second locking arm, and allowing a biasing member to transition the first locking arm and the second locking arm from an unlocked position to a locked position.

23. The method according to claim 22, wherein the first locking arm and the second locking arm are slidably engaged with the load cell along a second axis extending perpendicular to the first axis.

24. The method according to claim 22, further including actuating a release arm to transition the first locking arm and the second locking arm from the locked position to the unlocked position.

25. The method according to claim 17, wherein releasably securing the ring connector to the load cell includes a spring clip transition between a locked position and an unlocked position to engage a surface of a cradle disposed on the load cell.

26. The method according to claim 25, wherein the cradle includes a seat configured to support a bottom surface of the ring connector and transfer the force from the ring connector to the load cell.

* * * * *